United States Patent [19]

Pansiera

[11] Patent Number: 4,802,467

[45] Date of Patent: Feb. 7, 1989

[54] BI-CENTRIC KNEE JOINT SUPPORT

[76] Inventor: Timothy Pansiera, 1050 NW. First Ave., Boca Raton, Fla. 33432

[21] Appl. No.: 191,508

[22] Filed: May 9, 1988

[51] Int. Cl.⁴ .............................................. A61F 5/04
[52] U.S. Cl. ................................. 128/88; 128/80 C; 16/354; 623/39
[58] Field of Search ............... 128/80 C, 80 F, 80 R, 128/80 B, 80 J, 89 R, 89 A, 88; 16/354; 623/39

[56] References Cited

U.S. PATENT DOCUMENTS

| 887,369 | 5/1908 | Wilmot | 16/354 |
|---|---|---|---|
| 1,351,955 | 9/1920 | Lowry | 623/39 |
| 1,698,136 | 1/1929 | Lawrence | 16/354 |
| 3,954,023 | 5/1976 | Aguilar | 16/354 |
| 4,493,316 | 1/1985 | Reed et al. | 128/88 |
| 4,524,764 | 6/1985 | Miller et al. | 128/88 |
| 4,599,748 | 7/1986 | Garcia | 128/80 C |
| 4,614,454 | 9/1986 | Kassai | 16/354 |
| 4,633,867 | 1/1987 | Kausek | 128/88 |
| 4,643,176 | 2/1987 | Mason | 128/80 C |
| 4,684,158 | 8/1987 | Miclot | 16/354 |

Primary Examiner—Edgar S. Burr
Assistant Examiner—Huong Q. Pham
Attorney, Agent, or Firm—Melvin K. Silverman

[57] ABSTRACT

There is disclosed a bi-centric joint for use in an orthopedic support system which includes a plurality of interdigitating tubular elements, secured upon planar base means, in which hubs from which said tubular elements project are secured to proximal and distal sections of the orthopedic apparatus. The length of each interdigitating tubular radial spoke is such that, upon the passage of said spoke through a centerline defined by the centers of rotation of the hubs, a pivot action at the end of such spoke against a peripheral surface of said proximal or distal section will occur. The result is a simulation of natural movement of a human joint.

5 Claims, 2 Drawing Sheets

BI-CENTRIC KNEE JOINT SUPPORT

BACKGROUND OF THE INVENTION

The present invention relates to a joint having utility in orthotic braces in which it is desirable too obtain a fluid, but controlled, range of motion of a limb or joint which is supported by the orthotic brace.

The prior art, in the main, relates to knee joints for use in artificial limbs, as opposed to knee joints having use within an orthotic brace or other related support environment. Patents in the prior art, known to the inventor, consist of U.S. Pat. No. 1,124,220 (1915) to Gaines entitled knee joint for Artificial Limbs,; and U.S. Pat. No. 2,959,168 (1960) to Shook, entitled Knee Brace.

Further, there exists in the prior art a so-called double action ankle joint in which two bearings are employed, which bearings are held in a fixed position in respective races. This arrangement does not control or define the range of motion in the manner of my invention, as is set forth below.

While the above and other prior art disclose the use of gears within a joint of an orthotic device, nothing in the prior art known to the inventor makes use of elongate, cylindrical gear teeth employed as a means of controlling the character and range of motion of a distal element of a brace relative to a proximal element thereof. Accordingly, the invention as set forth herein is believed to represent a new concept in achieving fluid motion of an orthotic joint to thereby simulate the natural motion of a human limb or joint.

SUMMARY OF THE INVENTION

The present invention comprises a bi-centric joint for controlling the character and range of motion between distal and proximal sections of an orthotic support. More particularly, the inventive joint includes a planar base means upon which are rotationally mounted a first hub element and a second hub element. Said first hub element is integral to said proximal section of the orthotic device, and said second hub member is integral to the distal section of the orthotic support. Each hub is provided with a plurality of tubular gear teeth directed away from the center of the hub and secured on one side to a respective proximal or distal support member. Said tubular gear teeth are substantially equal in length to the distance between the peripheries of said hubs along the axis between said first and second hub. Said tubular gear teeth are positioned to interdigitate as rotation of said first hub relative to said second hub is induced by reason of movement of the limb of the patient that is in contact with said distal and proximal sections of the orthotic support. As such relative rotation occurs, said cylindrical teeth will move toward said lines defined by the centers of rotation of said first and second hubs. Further, said tubular gear teeth will pivot against the periphery of the opposite hub, thereby producing a characteristic movement of the rotation of said hubs relative to each other and, as well, providing support for the bicentric joint along said line between said centers of rotation of said hubs.

It is accordingly an object of present invention to provide a hinge for use in orthotic devices including, particularly, within knee braces, which will function to define a characteristic type of motion.

Another object is to provide a bi-centric orthotic joint which permits the natural joint of the patient to be flexed and otherwise moved in a fashion simulating that of natural movement.

It is of further object to provide an orthotic joint of the above type that will afford protection to the wearer against over-extension of the joint.

It is a yet further object to provide a joint of the above type that will provide a simulation of normal joint movement while affording protection to the patient against over-extension of the joint as the healing of an injury or correction of an orthopedic malfunction progresses.

The above and yet other objects and advantages of the present invention will become apparent from the hereinafter set forth detailed Description of the Invention, the Drawings, and Claims appended herewith.

DETAILED DESCRIPTION OF THE INVENTION

Figure 1:
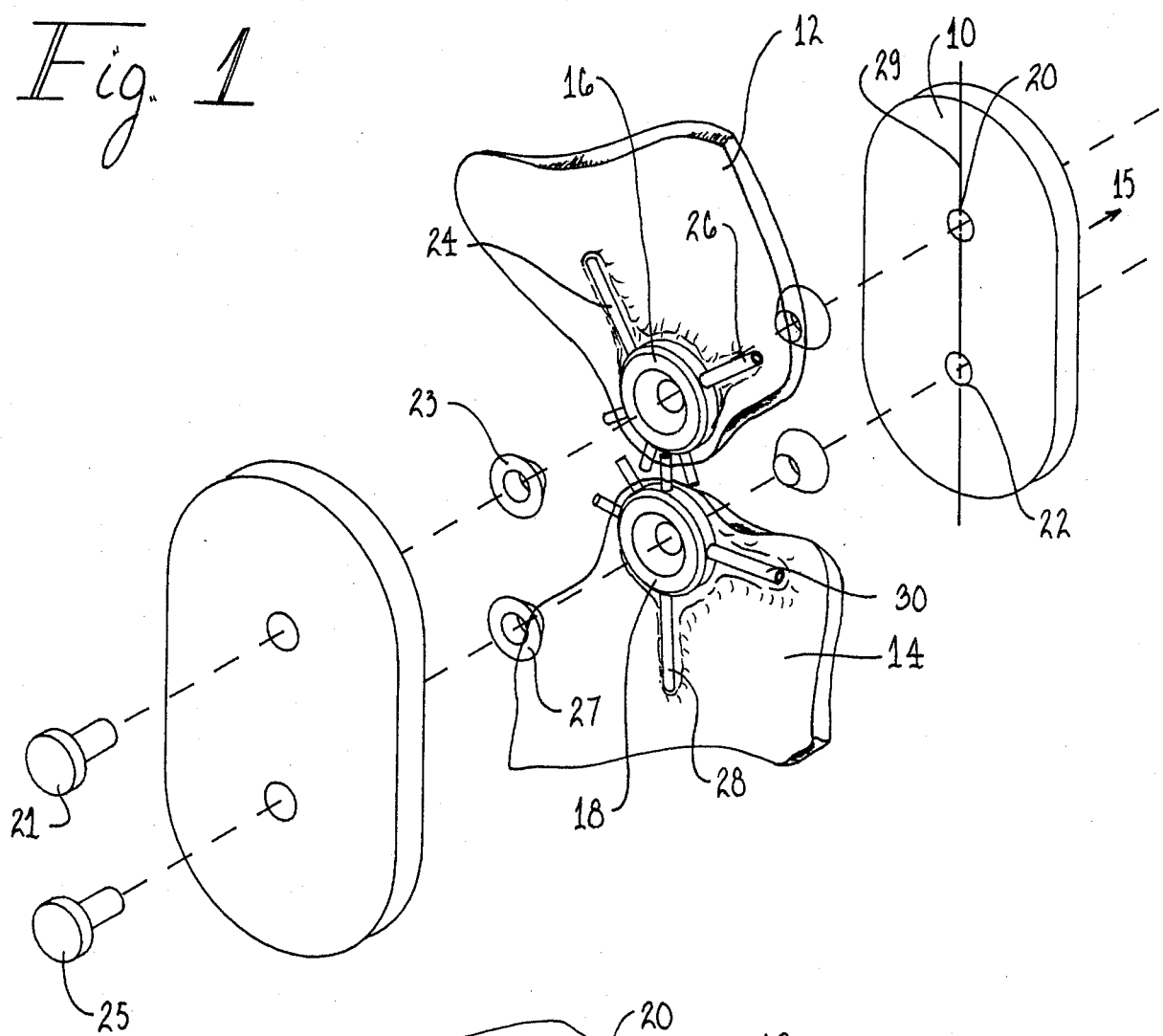
FIG. 1 is an exploded view of the hinge.

With reference to FIG. 1, there is shown a planner base means 10 having therein two holes which defined axes of rotation 20 and 22, as shown by the dotted lines in FIG. 11.

Further shown in FIG. 1 are proximal orthotic support member 12 and distal orthotic support member 14 of, for example, a knee brace or support. In such embodiment, the knee would be located in the direction shown by arrow 15.

Rotationally mounted upon said based means 10 is a first hub 16 and a second hub 18 which are secured to proximal and distal members 12 and 14 respectively through elongate elements 24, 26, 28 and 30 which, in one embodiment, are integrally molded within the material of which the proximal and distal members 12 and 14 are formed. It is to be appreciated that hubs 16 and 18 may be secured within proximal and distal members 12 and 14 by means other than through the use of elongate elements 24, 26, 28 and 30.

The rotational relationship of hub 16 and 18 relative to planar base means 10 is effectuated through the use of rivet 21 and bushing 23 as regards hub 16 and its axis of rotation 20, and of rivet 25 and bushing 27 with regard to hub 18 and its axis of rotation 22.

In FIG. 1 is also shown centerline 29 which is defined by the points at which axes 20 and 22 intersect base means 10.

Figure 2:
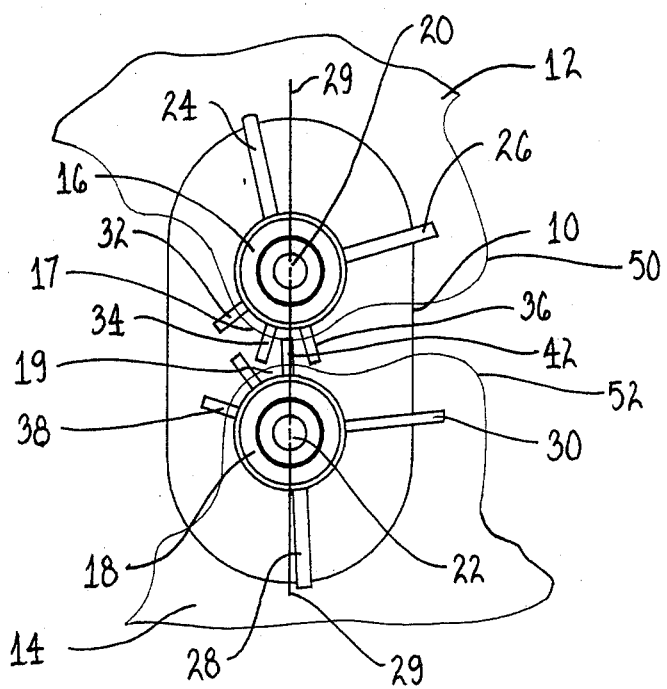
FIG. 2 is a radial schematic view of the center element of the hinge.

With reference to the radial schematic view of FIG. 1, it is seen that hub 16 is provided with tubular radial spokes 32, 34, and 36, while hub 22 is provided with tubular spokes 38, 40 and 42. In FIG. 2 it may be noted that the proximal and distal members 12 and 14 are provided with peripheral surfaces 17 and 19 respectively each having a recess (see FIG. 3) which are dimensioned such that each radial spoke will penetrate either peripheral surface 17 or 19 when such spoke passes through centerline 29 which, as above noted, is defined by the axes of rotation of hubs 16 and 18 on base means 10.

Figure 3:
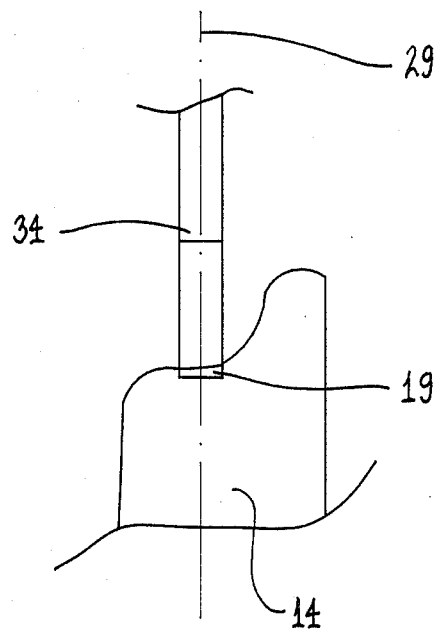
FIG. 3 is a cross-sectional view taken along the centerline of FIG. 2.

With further reference to FIG. 3, there is shown the relationship between tubular spoke 34 and the pivot point on peripheral surface 19 of distal member 14, when spoke 34 passes through centerline 29.

Accordingly, under the present invention there are defined interdigitating tubular gear teeth having a single contact point with the opposing gear structure such that stress between the respective gears are transmitted along the center line between the axes of rotation of the respective gears. In the present embodiment, such gears comprise hub 16 and 18 in combination with their tubular spokes.

It has been found that the above set forth use of a single contact point of a tubular spoke creates a rotational characteristic of the proximal member relative to the distal member which simulates that of a human joint. Further, the extent of the range of motion of a joint of the present type is defined by points 50 and 52 of the respective proximal and distal elements. Similar limit means may be formed, as may be desired in a given application, at the opposite side of the proximal and distal members.

Another characteristic of the present invention is that one of the tubular spokes gear teeth will, at all times, be substantial alignment with centerline 29 regardless of the position of the proximal support member relative to the distal support member. Accordingly, one tubular spoke, of the six illustrated, will always be in substantial alignment with the centerline thereby providing support for the brace under all relative angles of the proximal member relative to the distal member.

Accordingly, while there has been herein shown and described the preferred embodiment to the present invention it has been understood the present invention may be embodied otherwise than is herein illustrated and described that, within said embodiment, certain changes in the detail of construction and in the form and arrangement of the parts may be made without departing from the underlying idea or principles of this invention within the scope of the appended claims.

Having thus described my invention, what I claim a new, useful and non-obvious, and accordingly secured by Letters Patent of the United States is:

1. A bi-centric joint for an orthotic support device having proximal and distal members, the joint comprising:
   (a) planar base means having a first aperture and a second aperture, said planar base means having a longitudinal centerline;
   (b) a first hub, said hub being rotationally secured to said planar base means through said first aperture, said first aperture thereby defining an axis of rotation of said first hub, said first hub being integral to said proximal member along a peripheral edge of said first hub thereof;
   (c) a second hub, said second hub being rotationally secured to said planar base means through said second aperture, said second aperture thereby defining an axis of rotation of said second hub relative to said planar base, said second hub being integral to said distal member along a peripheral edge of said second hub thereof, said centerline passing through said rotational axes;
   (d) a plurality of spaced apart tubular radial spokes projecting radially outwardly from said first hub in the direction of said second hub; and
   (e) a plurality of spaced apart tubular radial spokes projecting radially outwardly from said second hub in the direction of said first hub, said respective pluralities of tubular radial spokes being in interdigitating relationship to each other, said spokes upon rotation of said hub sequentially passing in alignment with said centerline, each of said tubular spokes having a length such that, when each spoke is in alignment with said centerline, such spoke will penetrate a peripheral edge of said proximal or distal member to which the hub of such spoke is not rigidly secured, whereby a particular characteristic of relative movement between said first and second hubs, in the nature of a simulation of naturally occurring movement of a human joint, is obtained by the above combination of elements.

2. The bi-centric joint as recited in claim 1 in which said planar base means may comprise a flexible, resilient material.

3. The bi-centric knee joint as recited in claim 1 in which each of said pluralities of tubular spokes comprises three spokes.

4. The bi-centric joint as recited in claim 3 in which said rotational connection of said hubs to said planar base means comprises rivet and bushing mean extending through an axial opening in said hubs and through said apertures in said planar base means.

5. The bi-centric knee joint as recited in claim 1 in which said opposite peripheral surfaces of said proximal and distal members comprise recesses, for assuring stable movement of the said spoke thereacross.

* * * * *